United States Patent [19]

Van Lommen et al.

[11] Patent Number: 5,691,344
[45] Date of Patent: Nov. 25, 1997

[54] VASOCONSTRICTIVE SUBSTITUTED DIHYDROPYRANOPYRIDINES

[75] Inventors: Guy Rosalia Eugène Van Lommen, Berlaar, Belgium; Francisco Javier Fernández-Gadea, Toledo, Spain; José Ignacio Andrés-Gil, Madrid, Spain; Maria Encarnacion Matesanz-Ballesteros, Toledo, Spain

[73] Assignee: Janssen Pharmaceutica, N.V., Beerse, Belgium

[21] Appl. No.: 586,851

[22] PCT Filed: Aug. 12, 1994

[86] PCT No.: PCT/EP94/02700

§ 371 Date: Jan. 24, 1996

§ 102(e) Date: Jan. 24, 1996

[87] PCT Pub. No.: WO95/05381

PCT Pub. Date: Feb. 23, 1995

[30] Foreign Application Priority Data

Aug. 19, 1993 [EP] European Pat. Off. .............. 93202440

[51] Int. Cl.$^6$ ............... C07D 471/02; C07D 409/14; C07D 311/96; A61K 31/35

[52] U.S. Cl. ................ 514/269; 544/328; 544/331

[58] Field of Search ................. 544/328, 331; 514/269

[56] References Cited

U.S. PATENT DOCUMENTS

| | | | |
|---|---|---|---|
| 5,071,871 | 12/1991 | Blarer et al. | 514/456 |
| 5,137,901 | 8/1992 | Junge et al. | 514/373 |
| 5,140,031 | 8/1992 | Atwal et al. | 514/302 |
| 5,250,540 | 10/1993 | Arlt et al. | 514/302 |

FOREIGN PATENT DOCUMENTS

| | | |
|---|---|---|
| 0 352 613 | 1/1990 | European Pat. Off. . |
| 0 519 291 | 6/1992 | European Pat. Off. . |

*Primary Examiner*—Mukund J. Shah
*Assistant Examiner*—Tamthom T. Ngo
*Attorney, Agent, or Firm*—Charles J. Metz

[57] ABSTRACT

The present invention is concerned with compounds of formula

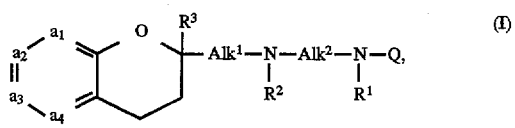

the pharmaceutically acceptable acid addition salts thereof, the N-oxides thereof and the stereochemically isomeric forms thereof, wherein $=a_1-a_2=a_3-a_4=$ is a bivalent radical of formula:

$$=N-CH=CH-CH= \qquad (a),$$

$$=CH-N=CH-CH= \qquad (b),$$

$$=CH-CH=N-CH= \qquad (c),$$

$$=CH-CH=CH-N= \qquad (d),$$

wherein in said bivalent radicals one or two hydrogen atoms can be substituted by halo, hydroxy, $C_{1-6}$alkyl or $C_{1-6}$alkyloxy; $R^1$ is hydrogen or $C_{1-6}$alkyl; $R^2$ is hydrogen or $C_{1-6}$alkyl; $R^3$ is hydrogen or $C_{1-6}$alkyl; $Alk^1$ is $C_{1-5}$alkanediyl; $Alk^2$ is $C_{2-15}$alkanediyl; Q is a five- or six-membered heterocyclic ring containing at least one nitrogen atom or a radical of formula

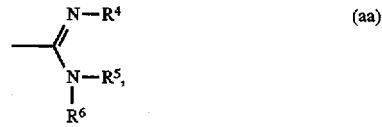

wherein $R^4$ is hydrogen, cyano, aminocarbonyl or $C_{1-6}$alkyl; $R^5$ is hydrogen, $C_{1-6}$alkyl, $C_{3-6}$alkenyl or $C_{3-6}$alkynyl; $R^6$ is hydrogen or $C_{1-6}$alkyl; or $R^5$ and $R^6$ taken together may form a bivalent radical of formula $-(CH_2)_4-$ or $-(CH_2)_5-$. Pharmaceutical compositions, preparations and use as a medicine are described.

13 Claims, No Drawings

VASOCONSTRICTIVE SUBSTITUTED DIHYDROPYRANOPYRIDINES

CROSS-REFERENCE TO RELATED APPLICATIONS

This application is based upon PCT Application Ser. No. PCT/EP 94/02700, filed Aug. 12, 1994, which claims priority from European Patent Application Serial No. 93.202.440.9, filed on Aug. 19, 1993.

The present invention relates to novel substituted dihydropyranopyridines, processes for their preparations, pharmaceutical compositions containing them and their use as a medicine, in particular for the prevention or treatment of disorders characterized by excessive vasodilatation, especially migraine.

Migraine is a non-lethal disease suffered by one in ten individuals. The main symptom is headache; other symptoms include vomiting and photophobia. For many years the most widely used treatment for migraine involved the administration of ergotalkaloids, which show however several adverse side effects. Recently a tryptamine derivative, i.e. sumatriptan, was introduced as a novel antimigraine drug. We have now surprisingly found that the present novel substituted dihydropyranopyridines show 5-$HT_1$-like agonistic activity and can thus be used in the treatment of disorders characterized by excessive vasodilatation, especially migraine.

The present invention is concerned with compounds of formula

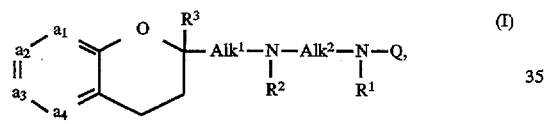   (I)

the pharmaceutically acceptable acid addition salts thereof, the N-oxides thereof and the stereochemically isomeric forms thereof, wherein =$a_1$—$a_2$=$a_3$—$a_4$= is a bivalent radical of formula:

=N—CH=CH—CH=    (a),

=CH—N=CH—CH=    (b),

=CH—CH=N—CH=    (c),

=CH—CH=CH—N=    (d), wherein in said bivalent radicals one or two hydrogen atoms can be substituted by halo, hydroxy, $C_{1-6}$alkyl or $C_{1-6}$alkyloxy;

$R^1$ is hydrogen or $C_{1-6}$alkyl;
$R^2$ is hydrogen or $C_{1-6}$alkyl;
$R^3$ is hydrogen or $C_{1-6}$alkyl;
$Alk^1$ is $C_{1-5}$alkanediyl;
$Alk^2$ is $C_{2-15}$alkanediyl;
Q is a radical of formula

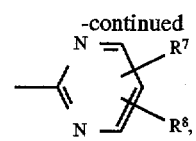   (aa)

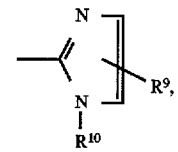   (bb)

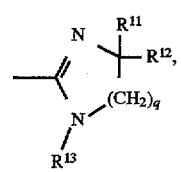   (cc)

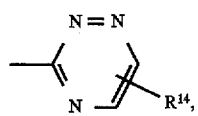   (dd)

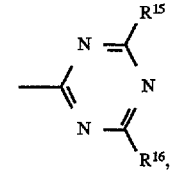   (ee)

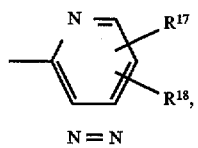   (ff)

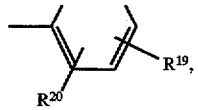   (gg)

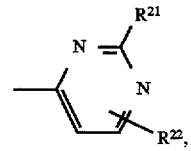   (hh)

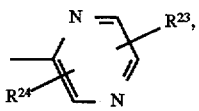   (ii)

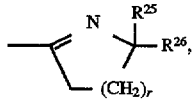   (jj)

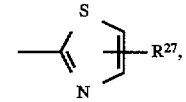   (kk)

(ll)

wherein
$R^4$ is hydrogen, cyano, aminocarbonyl or $C_{1-6}$alkyl;
$R^5$ is hydrogen, $C_{1-6}$alkyl, $C_{3-6}$alkenyl or $C_{3-6}$alkynyl;
$R^6$ is hydrogen or $C_{1-6}$alkyl; or
$R^5$ and $R^6$ taken together may form a bivalent radical of formula —$(CH_2)_4$— or —$(CH_2)_5$—;

$R^7$ and $R^8$ each independently are hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;

$R^9$ is hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;

$R^{10}$ is hydrogen, $C_{1-6}$alkyl, $C_{1-6}$alkylcarbonyl, or aryl $C_{1-6}$alkyl;

$R^{11}$ and $R^{12}$ are hydrogen or taken together with the carbon atom to which they are connected form C(O);

q is 1 or 2;

$R^{13}$ is hydrogen, $C_{1-6}$alkyl, $C_{1-6}$alkylcarbonyl, or aryl$C_{1-6}$alkyl;

$R^{14}$ is hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl) amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;

$R^{15}$ and $R^{16}$ each independently are hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;

$R^{17}$ and $R^{18}$ each independently are hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;

$R^{19}$ and $R^{20}$ each independently are hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;

$R^{21}$ and $R^{22}$ each independently are hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;

$R^{23}$ and $R^{24}$ each independently are hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;

r is 1 or 2;

$R^{25}$ and $R^{26}$ are hydrogen or taken together with the carbon atom to which they are connected form a C(O);

$R^{27}$ is hydrogen, halo or $C_{1-6}$alkyl, and aryl is phenyl optionally substituted with halo, hydroxy, $C_{1-6}$alkyl or $C_{1-6}$alkyloxy.

Some of the compounds of formula (I) may also exist in their tautomeric forms. Such forms although not explicitly indicated in the above formula are intended to be included within the scope of the present invention.

As used in the foregoing definitions halo defines fluoro, chloro, bromo and iodo; $C_{1-6}$alkyl defines straight and branch chained saturated hydrocarbon radicals having from 1 to 6 carbon atoms such as, for example, methyl, ethyl, propyl, butyl, pentyl, hexyl and the like; $C_{3-6}$alkenyl defines straight and branch chained hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl and the like; and the carbon atom of said $C_{3-6}$alkenyl being connected to a nitrogen atom preferably is saturated, $C_{3-6}$alkynyl defines straight and branch chained hydrocarbon radicals containing one triple bond and having from 3 to 6 carbon atoms such as, for example, 2-propynyl, 3-butynyl, 2-butynyl, 2-pentynyl, 3-pentynyl, 3-hexynyl, and the like; and the carbon atom of said $C_{3-6}$alkynylradical being connected to a nitrogen atom preferably is saturated; $C_{3-6}$cycloalkyl is generic to cyclopropyl, cyclobutyl, cyclopentyl and cyclohexyl; $C_{1-5}$alkanediyl defines bivalent straight and branch chained saturated hydrocarbon radicals having form 1 to 5 carbon atoms, such as, for example, methylene, 1,2-ethanediyl, 1,3-propanediyl, 1,4-butanediyl, 1,5-pentanediyl and the branched isomers thereof; $C_{2-15}$alkanediyl defines bivalent straight and branch chained saturated hydrocarbon radicals having from 2 to 15 carbon atoms such as, for example, 1,2-ethanediyl, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl, 1,13-tridecanediyl, 1,14-tetradecanediyl, 1,15-pentadecanediyl and the branched isomers thereof. The term "C(O)" refers to a carbonyl group.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term addition salt also comprises the hydrates and solvent addition forms which the compounds of formula (I) are able to form. Examples of such forms are e.g. hydrates, alcoholates and the like.

The term "stereochemically isomeric forms" as used hereinbefore defines all the possible isomefic forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; and $C_{3-6}$-alkenyl radicals may have the E- or Z-configuration. Stereochemically isomeric forms of the compounds of formula (I) are intended to be embraced within the scope of this invention.

The radical "=$a_1$—$a_2$=$a_3$—$a4$=" is suitably a radical of formula (a) or (c);

$R^1$ is suitably methyl or hydrogen, preferably $R^1$ is hydrogen;

$R^2$ is suitably methyl or hydrogen, preferably $R^2$ is hydrogen;

$R^3$ is suitably methyl or hydrogen, preferably $R^3$ is hydrogen;

$Alk^1$ is suitably $C_{1-3}$alkanediyl, preferably $Alk^1$ is methylene;

$Alk^2$ is suitably $C_{2-6}$alkanediyl, preferably $Alk^2$ is 1,3-propanediyl or 1,4-butanediyl;

Q is preferably a radical of formula (aa), (bb), (dd), (gg) or (ii);

$R^4$ is suitably hydrogen, cyano, aminocarbonyl or methyl, preferably $R^4$ is hydrogen or cyano;

$R^5$ is suitably hydrogen or $C_{1-6}$alkyl, preferably $R^5$ is hydrogen, methyl, ethyl or propyl;

$R^6$ is suitably hydrogen or $C_{1-6}$alkyl, preferably $R^6$ is hydrogen or methyl;

$R^7$ and $R^8$ each independently are suitably hydrogen, hydroxy, halo or methyl, preferably both $R^7$ and $R^8$ are hydrogen or $R^7$ is hydrogen and $R^8$ is hydroxy;

$R^9$ is suitably hydrogen, hydroxy, preferably $R^9$ is hydrogen;

$R^{10}$ is suitably hydrogen, or phenylmethyl, preferably $R^{10}$ is hydrogen;

q is preferably 2;

$R^{11}$ and $R^{12}$ are both preferably hydrogen;

$R^{13}$ is suitably hydrogen or phenylmethyl, preferably $R^{13}$ is hydrogen;

$R^{14}$ is suitably hydrogen, halo or methyl, preferably $R^{14}$ is hydrogen or chloro;

$R^{15}$ and $R^{16}$ each independently suitably are hydrogen, halo or methyl, preferably $R^{15}$ and $R^{16}$ are hydrogen or chloro;

$R^{17}$ and $R^{18}$ each independently suitably are hydrogen, hydroxy, chloro or methyl, preferably $R^{17}$ and $R^{18}$ are both hydrogen or $R^{17}$ is hydrogen and $R^{18}$ is hydroxy;

$R^{19}$ and $R^{20}$ each independently suitably are hydrogen, hydroxy, halo or methyl, preferably $R^{19}$ and $R^{20}$ are both hydrogen or $R^{19}$ is hydrogen and $R^{20}$ is chloro;

$R^{21}$ and $R^{22}$ each independently suitably are hydrogen, halo, $C_{1-6}$alkyloxy, $C_{1-6}$alkylthio, amino, mono- or di($C_{1-6}$alkyl)amino, preferably $R^{21}$ is hydrogen, chloro, methylthio or amino and $R^{22}$ is hydrogen;

$R^{23}$ and $R^{24}$ each independently suitably are hydrogen, halo or $C_{1-6}$alkyl, preferably $R^{23}$ and $R^{24}$ are hydrogen or chloro;

r preferably is 2;

$R^{25}$ and $R^{26}$ both preferably are hydrogen;

$R^{27}$ is suitably hydrogen or methyl, preferably $R^{27}$ is hydrogen; and aryl is preferably phenyl.

Interesting compounds are those compounds of formula (I), wherein $R^1$ and $R^2$ both are hydrogen.

Also interesting compounds are those compounds of formula (I), wherein $=a_1-a_2=a_3-a_4=$ is a bivalent radical of formula (a).

Another goup of interesting compounds are those compounds of formula (I), wherein $=a_1-a_2=a_3-a_4=$ is a bivalent radical of formula (c).

Particular compounds are those interesting compounds of formula (I), wherein Q is a radical of formula (aa), (bb), (dd), (gg) or (ii), especially (bb), (dd), (gg) or (ii).

Particularly interesting compounds are those interesting compounds, wherein Q is a radical of formula (bb), $R^7$ and $R^8$ are both hydrogen.

Another group of particularly interesting compounds are those interesting compounds, wherein Q is a radical of formula (dd), $R^{11}$, $R^{12}$ and $R^{13}$ are hydrogen and q is 2.

Yet another group of particularly interesting compounds are those interesting compounds wherein Q is a radical of formula (gg), $R^{17}$ and $R^{18}$ are hydrogen.

Still another group of particularly interesting compounds are those interesting compounds wherein Q is a radical of formual (ii), $R^{21}$ is methylthio and $R^{22}$ is hydrogen.

Preferred compounds are:

N-[(3,4-dihydro-2H-pyrano[2,3-b]-pyridin-2-yl)methyl]-N'-2-pyrimidinyl-1,3-propanediamine; N-[(3,4-dihydro-2H-pyrano[2,3-b]pyridin-2-yl)methyl]-N'-(1,4,5,6-tetrahydro-2-pyrimidinyl)-1,3-propanediamine; N-[(3,4-dihydro-2H-pyrano[2,3-b]pyridin-2-yl)methyl]-N'-2-pyrimidinyl-1,3-propanediamine, N-oxide; N-[(3,4-dihydro(2H)pyrano(3,2-c)pyridin-2-yl)methyl]-N'-2-pyrimidinyl-1,3-propanediamine; N-[(3,4-dihydro-2H-pyrano[2,3-b]pyridin-2-yl)methyl]-N'-[2-(methylthio)-4-pyrimidinyl]-1,3-propanediamine; N-[(3,4-dihydro-2H-pyrano[2,3-b]pyridin-2-yl)methyl]-N'-2-pyridinyl-1,3-propanediamine; and N"-cyano-N-[3-[[(3,4-dihydro-2H-pyrano[2,3-b]pyridin-2-yl)methyl]amino]propyl]-N'-propylguanidine;

the pharmaceutically acceptable acid addition salts or the stereochemically isomeric forms thereof.

The compounds of formula (I) can generally be prepared by reacting a diamine of formula (II) with a reagent of formula (III). In the formulas (II), (III) and all the following formulas the variabels "$=a_1a_2=a_3-a_4=$", $R^1$, $R^2$, $R^3$, $Alk^1$, $Alk^2$, and Q are as defined under formula (I). In formula (III) $W^1$ is a reactive leaving group such as, for example, halo, e.g. chloro, bromo; alkyloxy, e.g. methoxy, ethoxy and the like; aryloxy, e.g. phenoxy and the like; alkylthio, e.g. methylthio, ethylthio and the like; arylthio, e.g. benzenethio and the like.

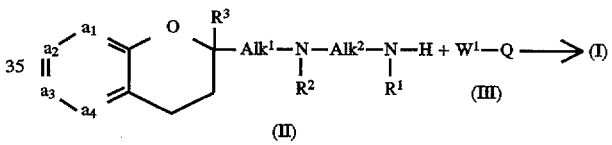

(II)  (III)

Said reaction can be performed by stirring the diamine of formula (II) with the reagent of formula (III) optionally in an appropriate solvent such as, for example, an alcohol, e.g. ethanol and the like; a halogenated hydrocarbon, e.g. trichloromethane and the like; an ether, e.g. tetrahydrofuran and the like; an aromatic hydrocarbon, e.g. methylbenzene and the like or mixtures thereof. Optionally a base, such as, for example, an alkalimetal carbonate, e.g. sodium or potassium carbonate; an alkalimetal hydrogen carbonate, e.g. sodium or potassium hydrogen carbonate; an appropriate organic base, e.g. N,N-diethylethanamine, pyridine and the like bases, can be added to pick up the acid that may be formed during the course of the reaction. Elevated temperatures may enhance the rate of the reaction. Preferably the reaction is performed at the reflux temperature of the reaction mixture.

The compounds of formula (I) can also generally be prepared by reductive N-alkylation of an aminoderivative of formula (VI) with an appropriate aldehyde of formula (V), wherein $Alk^3$ is a direct bond or $C_{1-4}$alkanediyl.

(IV)

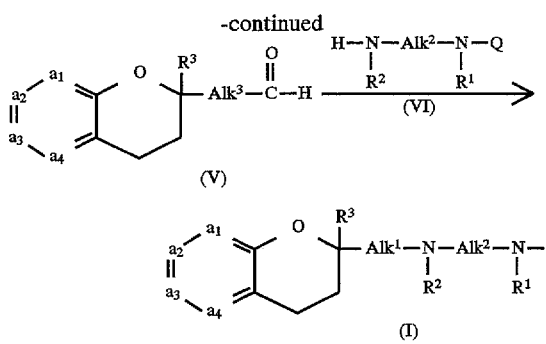

(V)

(I)

Said reaction is performed by stirring the reactants in an appropriate solvent such as, for example, an alcohol, e.g. ethanol and the like; an ether, e.g. tetrahydrofuran and the like; an aromatic solvent, e.g. methylbenzene and the like, or mixtures thereof. Optionally a water separator can be used to remove the water that is formed during the course of the reaction. The resulting imine can then be reduced by reactive hydride reagents such as, for example, sodium borohydride, or by catalytic hydrogenation on an appropriate catalyst, such as, for example palladium on charcoal, platinum on charcoal, Raney nickel and the like in a suitable solvent such as, for example an alcohol, e.g. methanol, ethanol and the like; an ether, e.g. tetrahydrofuran and the like; a carboxylic ester, e.g. ethyl acetate, butyl acetate and the like; or a carboxylic acid, e.g. acetic acid, propanoic acid and the like. Optionally the reaction may be performed at elevated temperatures and/or pressures.

The intermediate aldehyde of formula (V) can be prepared by reducing an acyl derivative of formula (IV) wherein Alk$^3$ is defined as above and Y is halo. The acyl halide can be prepared by reacting the acid of formula (IV) wherein Y is OH, with a halogenating reagent such as thionylchloride, phosphorus trichloride, phosphorus tribromide, oxalylchloride and the like. The latter reaction may be performed in an excess of the halogenating reagent or in appropriate solvents such as for example halogenated hydrocarbons, e.g. dichloromethane, trichloromethane and the like; aromatic hydrocarbons, e.g. methylbenzene and the like; ethers, e.g. tetrahydrofuran, 1,4-dioxane and the like; or dipolar aprotic solvents, e.g. N,N-dimethylformamide, N,N-dimethylacetamide and the like. Stirring and elevated temperatures may be appropriate to enhance the rate of the reaction. Said reduction of the acylhalide of formula (IV) can for instance be performed by catalytic hydrogenation with a catalyst such as palladium on charcoal, palladium on bariumsulfate, platinum on charcoal and the like in appropriate solvents such as, for example ethers, e.g. tetrahydrofuran and the like; preferably in admixture with a dipolar aprotic solvent, such as, for example N,N-dimethylformamide, N,N-dimethylacetamide and the like. Optionally a catalyst poison can be added, such as thiophene, quinoline/sulfur and the like. The reaction sequence starting from the intermediate of formula (IV) and yielding compounds of formula (I) may be performed as a one-pot procedure.

The compounds of formula (I) may also be prepared by N-alkylating an amine of formula (VI) with an intermediate of formula (VII), wherein W$^2$ is a reactive leaving group such as, for example, halo, e.g. chloro, bromo or iodo; sulfonyloxy, e.g. methanesulfonyloxy, methylbenzenesulfonyloxy and the like, optionally in appropriate solvents such as ketones, e.g. 2-butanone and the like; ethers, e.g. tetrahydrofuran and the like; aromatic hydrocarbons, e.g. methylbenzene and the like; dipolar aprotic solvents, e.g. N,N-dimethylformamide, N,N-dimethylacetamide, dimethylsulfoxide and the like.

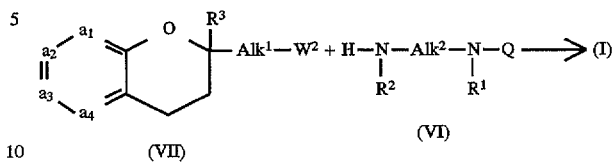

(VII)         (VI)

Stirring and heating may enhance the reaction rate. Optionally a suitable base may be added to pick up the acid that is formed during the course of the reaction such as, for example an alkali metal carbonate, e.g. sodium or potassium carbonate; an alkali metal hydrogen carbonate, e.g. sodium or potassium hydrogen carbonate and the like; an appropriate organic base, e.g. N,N-diethylethanamine, pyridine and the like.

The compounds of formula (I), can also be converted into each other by functional group transformations. For instance the compounds of formula (I), wherein Q represents a pyrimidinyl moiety, can be converted into the tetrahydroanalogs following art-known catalytic hydrogenation procedures.

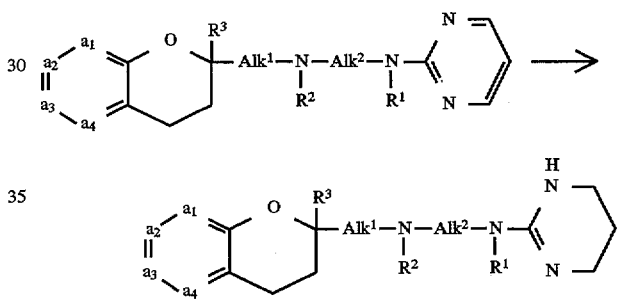

Furthermore, compounds of formula (I) bearing a $C_{3-6}$alkynylgroup or $C_{3-6}$alkenylgroup can be converted into the corresponding compounds bearing $C_{1-6}$alkylgroup following art-known hydrogenation techniques. Compounds of formula (I) bearing a cyanogroup can be convened into the corresponding compounds bearing an aminomethyl substituent following art-known hydrogenation techniques. Compounds bearing an alkyloxy substituent can be converted into compounds bearing a hydroxy group by treating the alkyloxy compound with an appropriate acidic reagent such as for example, hydrohalic acid, e.g. hydrobromic acid or borontribromide and the like. Compounds bearing an amino substituent can be N-acylated or N-alkylated following art-known N-acylation or N-alkylation procedures. The N-oxides of the compounds formula (I) may also be prepared following art-known methods.

Intermediates of formula (VII), wherein "=$a_1$—$a_2$=$a_3$—$a_4$=" is a bivalent radical of formula (a) have been described in Arlt et al, U.S. Pat. No. 5,250,540, filed on Jun. 11, 1992, and issued on Oct. 5, 1993.

Intermediates of formula (VII), wherein "=$a_1$—$a_2$=$a_3$—$a_4$=" is a bivalent radical of formula (c), Alk$^1$ is a methylene and W$^2$ is a reactive leaving group, especially halo, may for instance be prepared as described hereinunder as Example 2 of the Experimental part. These intermediates are represented by formula (VII-c).

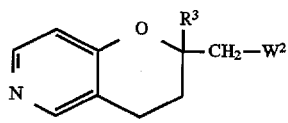 (VII-c)

Other intermediates are novel and can be prepared following art-known procedure.

Pure stereochemically isomeric forms of the compounds of this invention may be obtained by the application of art-known procedures. Diastereoisomers may be separated by physical separation methods such as selective crystallization and chromatographic techniques, e.g. liquid chromatography. Enantiomers may be separated from each other by the selective crystallization of their diastereomeric salts with optically active acids. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials. Stereochemically isomeric forms of the compounds of formula (I) are obviously intended to be included within the scope of the invention.

The compounds of formula (I), the pharmaceutically acceptable acid-addition salts and stereochemically isomeric forms thereof have interesting pharmacological properties: they show $5HT_{1-like}$ agonistic activity. The compounds of the present invention have a remarkable vasoconstrictor activity. They are useful to prevent and treat conditions which are related to vasodilatation. For instance, they are useful in the treatment of conditions characterized by or associated with cephalic pain, e.g. cluster headache and headache associated with vascular disorders, especially migraine. These compounds are also useful in the treatment of venous insufficiency and in the treatment of conditions associated with hypotension. The vasoconstrictor activity of the compounds of formula (I) can be determined using an in vitro-test as is described in "Instantaneous changes of alpha-adrenoreceptor affinity caused by moderate cooling in canine cutaneous veins" in the American Journal of Physiology 234(4), H330-H337, 1978; or in the test described in the pharmacological example, wherein the serotonin-like response of the compounds of the present invention was tested on the basilar arteries of pigs.

In view of their useful pharmacological properties, the subject compounds may be formulated into various pharmaceutical forms for administration purposes. To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carders such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of the present invention therefore may be used as medicines in conditions related to vasodilatation, more in particular hypotension, venous insufficiency and especially cephalic pain among which migraine. The compounds of the present invention also provide a method of treating warm-blooded animals suffering from conditions related to vasodilatation, such as, hypotension, venous insufficiency and especially cephalic pain among which migraine by administering an effective amount of a compound of formula (I), a pharmaceutically acceptable acid addition salt or a stereoisomeric form thereof. Those skilled in the an could easily determine the effective amount from the test results presented hereinafter. In general it is contemplated that an effective amount would be from 1 µg/kg to 1 mg/kg body weight, and in particular from 2 µg/kg to 200 µg/kg body weight. It may be appropriate to administer the required dose as two, three, four or more sub-doses at appropriate intervals throughout the day. Said sub-doses may be formulated as unit dosage forms, for example, containing 0.005 to 20 mg, and in particular 0.1 mg to 10 mg of active ingredient per unit dosage form.

The following examples are intended to illustrate and not to limit the scope of the present invention in all its aspects.

EXPERIMENTAL PART

A) Preparation of the Intermediate Compounds

EXAMPLE 1

3-chlorobenzenecarboperoxoic acid (0.0153 mol) was added portionwise to 2-(chloromethyl)-3,4-dihydro-2 H-pyrano[2,3-b]pyridine (0.0153 mol) in trichloromethane (100 ml) and the mixture was stirred at room temperature for 2 hours. The mixture was washed with a saturated sodium hydrogen carbonate solution and extracted. The organic layer was dried ($Na_2SO_4$), filtered off and evaporated till dryness. The residue was purified by an open column chromatography over silica gel (eluent: $CH_2Cl_2/CH_3OH$ 98/2, 96/4, 90/10 and 80/20). The pure fractions were collected and evaporated. The product was used without further purification, yielding 2.16 g (70%) of (±)-2-(chloromethyl)-3,4-dihydro-2H-pyrano[2,3-b]pyridine,8-oxide (interm. 1).

EXAMPLE 2 a) A mixture of aluminum (0.137 mol) and $HgCl_2$ (0.012 g) in tetrahydrofuran (100 ml) was stirred and heated under nitrogen atmosphere at 40° C. 3-bromo-2-propenyl (0.2265 mol) in tetrahydrofuran (100 ml) was added carefully and the mixture was stirred at 60° C. for 1 hour. The mixture was cooled till −60° C. and 4-methoxy-3-pyridinecarboxaldehyde (0.0985 mol) in tetrahydrofuran (100 ml) was added dropwise. The mixture was stirred at 0° C. for 1 hour and then at 20° C. for 2 hours. The mixture was treated with aqueous $NH_4Cl$, stirred for 30 minutes, filtered off and the filtrate was evaporated till dryness. Water was added and the mixture was extracted with EtOAc. The organic layer was discarded. The aqueous layer was basified, extracted with EtOAc, dried ($Na_2SO_4$), filtered off and evaporated till dryness. The product was used without further purification, yielding: 13.5 g (76%) (±)-4-methoxy-α-(2-propenyl)-3-pyridinemethanol (interm. 2).

b) Thionyl chloride (0.456 mol) was added dropwise to a solution of intermediate 2 (0.0456 mol) in dichloromethane (150 ml) and the mixture was stirred at room temperature overnight. The mixture was evaporated till dryness, the residue was washed with a saturated sodium hydrogen carbonate solution and extracted with dichloromethane. The organic layer was dried ($Na_2SO_4$), filtered off and evaporated till dryness. The product was used without further purification, yielding 10 g (89%) (±)-3-(1-chloro-3-butenyl)-4-methoxypyridine (interm. 3).

c) A mixture of intermediate 3 (0.0405 mol) and Zn (0.1591 mol) in acetic acid (400 ml) was stirred at room temperature for 1 h. The mixture was filtered off and he filtrate was evaporated till dryness. The residue was washed with NaOH 10% and extracted with $CH_2Cl_2$. The organic layer was dried ($Na_2SO_4$), filtered off and evaporated till dryness. The residue (7 g) was purified by short open column chromatography over silica gel (eluent: $CH_2Cl_2/CH_3OH$ 97/3). The pure fractions were collected and the eluent was evaporated. The product was used without further purification, yielding: 4 g (60%) of 3-(3-butenyl)-4-methoxypyridine (interm. 4).

d) A mixture of bis(trimethylsilyl)sulphate (0.0318 mol) and sodium methoxide (0.0278 mol) in 1,3-dimethyl-2-imidazolidinone (50 ml) was stirred under $N_2$ for 1 h. Intermediate 4(0.0184 mol) in 1,3-dimethyl-2-imidazolidinone (10 ml) was added and the mixture was stirred at 150° C. for 4 h. The mixture was washed with a saturated solution of $NH_4Cl$ and extracted with $CH_2Cl_2$. The organic layer was dried ($Na_2SO_4$), filtered off and evaporated till dryness. The product was used without further purification, yielding: 1.4 g (51%) 3-(3-butenyl)-4-pyridinol (interm. 5).

A mixture of intermediate 5 (0.01 mol) in trichloromethane (100 ml) was cooled on an ice bath. Bromine (0.01 mol) in trichloromethane (50 ml) was added dropwise and the mixture was stirred at room temperature for 1 h. N,N-diethylethanamine (40 ml) was added and the mixture was stirred at 100° C. for 3 h. The mixture was evaporated till dryness and the residue was purified by short open column chromatography over silica gel (eluent: $CH_2Cl_2/CH_3OH$ 97/3). The pure fractions were collected and evaporated, yielding 1.2 g (52%) (±)-2-bromomethyl-3,4-dihydro(2H)pyrano(3,2-c)pyridin (interm. 6).

B) Preparation of the Final Compounds

EXAMPLE 3

2-(bromomethyl)-3,4-dihydro-(2H)-pyrano[2,3-b] pyridine (0.0156 mol) and N-2-pyrimidinyl-1,3-propanediamine (0.0312 mol)were stirred at 100° C. for 1.5 hours. The mixture was purified first by open column chromatography over silica gel (eluent: $CH_2Cl_2/CH_3OH$ 90/10) and then by HPLC over silica gel (eluent: $CH_2Cl_2/$($CH_3OH/NH_3$) 95/5). The pure fractions were collected and evaporated. The oily residue was converted into the hydrochloric acid salt (1:3) in 1,1'-oxybisethane/2-propanol, yielding 1.8 g (25%) of (±)-N-[(3,4-dihydro-2H-pyrano[2,3-b]-pyridin-2-yl)methyl]-N'-2-pyrimidinyl-1,3-propanediamine trihydrochloride. 2-propanolate(1:1). monohydrate; mp. 119.3° C. (comp. 1).

EXAMPLE 4

A mixture of compound (1) (0.0047 mol) and hydrochloric acid in 2-propanol (0.0205 mol) in methanol (45 ml) was hydrogenated at room temperature under normal pressure in a Parr apparatus with palladium on activated carbon (0.43 g) as a catalyst. After uptake of hydrogen (2 eq.), the catalyst was filtered off and the filtrate was evaporated till dryness. The residue was purified by an open column chromatography over silica gel (eluent: $CH_2Cl_2$/($CH_3OH/NH_3$) 9/1). The pure fractions were collected and evaporated. The residue was converted into the hydrochloric acid salt (2:5) in 2-propanol and evaporated till dryness. The residue was dried with $P_2O_5$ and KOH, yielding 0.93 g (43%) of N-[(3,4-dihydro-2H-pyrano[2,3-b]pyridin-2-yl)methyl]-N'-(1,4,5,6-tetrahydro-2-pyrimidinyl)-1,3-propanediamine dihydrochloride. 2-propanolate (2:1). monohydrate; mp. 143.3° C. (comp. 2).

EXAMPLE 5

A mixture of 0.01 mol of intermediate 1 and 0.0315 mol of N-2-pyrimidinyl-1,3-propanediamine were stirred at 100° C. for 90 minutes. The mixture was purifed first by two flash chromatographies over silica gel (eluent: $CH_2Cl_2$/($CH_3OH/NH_3$) 9/1) and then by HPLC (eluent: $CH_2Cl_2$/($CH_3OH/NH_3$) 9/1). The pure fractions were collected and evaporated. The residue was converted into the ethanedioic acid salt (2:1) in $C_2H_5OH$, yielding 0.43 g (12%) of (±)-N-(3,4-dihydro-2H-pyrano[2,3-b]pyridon-2-yl)methyl]-N'-2-pyrimidinyl-1,3-propanediamine, N-oxide ethanedioate (2:1). monohydrate; mp. 108.0° C. (comp. 3).

EXAMPLE 6

A mixture of 0.0053 mol of intermediate 6 and 0.0105 mol of N-2-pyrimidinyl-1,3-propanediamine were stirred at 100° C. for 2 hours. The mixture was purifed by column chromatography over silica gel (eluent: $CH_2Cl_2$/($CH_3OH/NH_3$) 95/5) and then by HPLC over silica gel (eluent: hexane/$CH_2Cl_2$/($CH_3OH/NH_3$) 5/4.5/0.5). The pure fractions were collected and evaporated. The residue was further purified by column chromatography NH2 KROMASIC I.D.: 2.5 cm JOUR (15 μm) (eluent: $CH_2Cl_2$/($CH_3OH$ 96.5/3.5) injection 9×0.1 g dissolved in 10 ml of eluent. The pure fractions were collected and evaporated. The residue was dissolved in methanol (30 ml) and converted into the ethanedioic acid salt (2:5). The precipitate was filtered off and dried in vacuo, yielding 0.4 g (14%) of (R 104542); top. 185.2° C. (±)-N-[(3,4-dihydro(2H)pyrano(3,2-c)pyridin-2-yl)methyl]-N'-2-pyrimidinyl-1,3-propanediamine ethanedioate (5:2) (comp. 4).

This procedure was repeated until stable responses were obtained. Subsequently the test compound was administered to the organ bath and the constriction of the preparation was

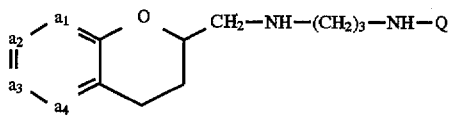

| Comp. no. | Ex. no. | =a1-a2=a3-a4- | Q | Physical data |
|---|---|---|---|---|
| 1 | 3 | =-N-CH=CH-CH= | N⟨N⟩ (pyrimidinyl) | 3HCl/H2O/ 2-propanolate (2:1) mp. 119.3° C. |
| 2 | 4 | =N-CH=CH-CH= | N⟨NH⟩ (imidazolyl) | 2HCl/H2O/ 2-propanolate (2:1) mp. 143.3° C. |
| 3 | 5 | =(N→O)-CH=CH-CH= | N⟨N⟩ | (COOH)₂ (2:1)/H2O mp. 108.0° C. |
| 4 | 6 | =CH-CH=N-CH= | N⟨N⟩ | (COOH)₂ (5:2) mp. 185.2° C. |
| 5 | 3 | =N-CH=CH-CH= | N⟨N⟩-SCH₃ | 3HCl/H2O/ 2-propanolate (2:1) mp. 234.2° C. |
| 6 | 3 | =N-CH=CH-CH= | N⟨⟩ (pyridyl) | (COOH)₂ (1:1)/ mp. 174.9° C. |
| 7 | 3 | =N-CH=CH-CH= | N⟨⟩ | 3HCl.7/2H2O/ mp. 165.9° C. |
| 8 | 3 | =N-CH=CH-CH= | N—CN ‖ —C—NH—C₃H₇ | (COOH)₂ (3:2) mp. 153.4° C. |

PHARMACOLOGICAL EXAMPLE

EXAMPLE 7

Segments of basilar arteries taken from pigs (anaesthetised with sodium pentobarbital) were mounted for recording of isometric tension in organ baths. The preparations were bathed in Krebs—Henseleit solution. The solution was kept at 37° C. and gassed with a mixture of 95% $O_2$–5% $CO_2$. The preparations were stretched until a stable basal tension of 2 grams was obtained.

The preparations were made to constrict with serotonin ($3\times10^{-7}$ M). The response to the addition of serotonin was measured and subsequently the serotonin was washed away. This procedure was repeated until stable responses were obtained. Subsequently the test compound was administered to the organ bath and the constriction of the preparation was measured. This constrictive response was expressed as a percentage of the response to serotonin as measured previously.

In table 3 the $IC_{50}$ concentrations of the compounds of formula (I) are presented.

TABLE 3

| Co. No. | IC$_{50}$(M) |
| --- | --- |
| 1 | 7.1 × 10$^{-8}$ |
| 2 | 1.3 × 10$^{-7}$ |
| 3 | 3.4 × 10$^{-7}$ |
| 5 | 2.6 × 10$^{-7}$ |
| 6 | 1.2 × 10$^{-7}$ |

D. COMPOSITION EXAMPLES

"Active ingredient" (A.I.) as used throughout these examples relates to a compound of formula (I), a pharmaceutically acceptable acid addition salt or a stereochemically isomeric form thereof.

EXAMPLE 8: ORAL DROPS

500 Grams of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 9: ORAL SOLUTION

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 10: CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient

EXAMPLE 11: FILM-COATED TABLETS

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE 12: INJECTABLE SOLUTION 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration (U.S.P. XVII p. 811) and filled in sterile containers.

EXAMPLE 13: SUPPOSITORIES

3 Grams A.I. was dissolved in a solution of 3 grams 2,3-dihydroxybutanedioic acid in 25 ml polyethylene glycol 400. 12 Grams surfactant (SPAN®) and triglycerides (Witepsol 555®) q.s. ad 300 grams were molten together. The latter mixture was mixed well with the former solution. The thus obtained mixture was poured into moulds at a temperature of 37°–38° C. to form 100 suppositories each containing 30 mg/ml of the A.I.

EXAMPLE 14: INJECTABLE SOLUTION

60 Grams of A.I. and 12 grams of benzylalcohol were mixed well and sesame oil was added q.s. ad 1 l, giving a solution comprising 60 mg/ml of A.I. The solution was sterilized and filled in sterile containers.

We claim:

1. A compound having the formula:

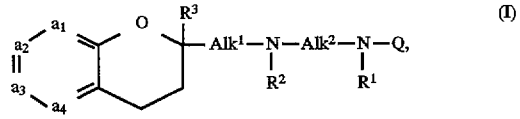

a pharmaceutically acceptable acid addition salt thereof, an N-oxide thereof or a stereochemically isomeric form thereof, wherein:

=a$_1$—a$_2$=a$_3$—a$_4$= is a bivalent radical of the formula:

| =N—CH=CH—CH= | (a); |
| --- | --- |
| =CH—N=CH—CH= | (b); |
| =CH—CH=N—CH= | (c); | or

| =CH—CH=CH—N= | (d), |
| --- | --- | wherein in said bivalent radical one or two hydrogen atoms can be replaced with halo, hydroxy, C$_{1-6}$alkyl or C$_{1-6}$alkyloxy;

R$^1$ is hydrogen or C$_{1-6}$alkyl;

R$^2$ is hydrogen or C$_{1-6}$alkyl;

$R^3$ is hydrogen or $C_{1-6}$alkyl;
$Alk^1$ is $C_{1-5}$alkanediyl;
$Alk^2$ is $C_{2-15}$alkanediyl; and
Q is a radical of the formula:

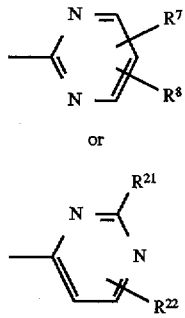

(bb)

or (ii)

wherein:

$R^7$ $R^8$ $R^{21}$ and $R^{22}$ each independently are hydrogen hydroxy, halo $C_{1-6}$alkyl, $C_{1-6}$alkyloxy, aryloxy, $C_{1-6}$alkylthio, cyano, amino, mono- or di ($C_{1-6}$alkyl) amino, mono- or di ($C_{3-6}$cycloalkyl) amino, aminocarbonyl, $C_{1-6}$alkyloxycarbonylamino, $C_{1-6}$alkylaminocarbonylamino, piperidinyl or pyrrolidinyl;

wherein in the foregoing, aryl is phenyl optionally substituted with halo, hydroxy, $C_{1-6}$alkyl or $C_{1-6}$alkyloxy.

2. A compound as claimed in claim 1 wherein $R^1$ and $R^2$ both are hydrogen and $Alk^2$ is 1,3-propanediyl.

3. A compound as claimed in claim 1 wherein =$a_1$—$a_2$=$a_3$—$a_4$= is a bivalent radical of formula (a) or (c).

4. A compound according to claim 1 wherein the compound is selected from the group consisting of:

N-[(3,4-dihydro-2H-pyrano[2,3-b]pyridin-2-yl)methyl]-N'-2-pyrimidinyl-1,3-propanediamine;

N-[(3,4-dihydro-2H-pyrano[2,3-b]pyridin-2-yl)methyl]-N'-2-pyrimidinyl-1,3-propanediamine,N-oxide;

N-[(3,4-dihydro-2H-pyrano[3,2-c]pyridin-2-yl)methyl]-N'-2-pyrimidinyl-1,3-propanediamine; and N-[(3,4-dihydro-2H-pyrano[2,3-b]pyridin-2-yl)methyl]-N'-[2-(methylthio)-4-pyrimidinyl]-1,3-propanediamine;

pharmaceutically acceptable acid addition salts thereof and stereochemically isomeric forms thereof.

5. A pharmaceutical composition containing a pharmaceutically acceptable carrier and as an active ingredient a therapeutically effective amount of a compound as claimed in claim 1.

6. A method for inducing vasoconstriction which comprises administering an effective vasoconstriction amount of a compound as defined in claim 1.

7. A method for inducing vasoconstriction which comprises administering an effective vasoconstriction amount of a compound as defined in claim 2.

8. A method for inducing vasoconstriction which comprises administering an effective vasoconstriction amount of a compound as defined in claim 3.

9. A method for inducing vasoconstriction which comprises administering an effective vasoconstriction amount of a compound as defined in claim 4.

10. A method for treating migraine which comprises administering an effective vasoconstriction amount of a compound as defined in claim 1.

11. A method for treating migraine which comprises administering an effective vasoconstriction amount of a compound as defined in claim 2.

12. A method for treating migraine which comprises administering an effective vasoconstriction amount of a compound as defined in claim 3.

13. A method for treating migraine which comprises administering an effective vasoconstriction amount of a compound as defined in claim 4.

* * * * *